United States Patent [19]

Pfund et al.

[11] Patent Number: 5,424,483
[45] Date of Patent: Jun. 13, 1995

[54] METHODS AND COMPOSITIONS OF A HYBRID GENETIC CORN COMPLEMENT, DK554

[75] Inventors: John H. Pfund, Sycamore, Ill.; James R. Larkins, Waldo, Ohio

[73] Assignee: Dekalb Plant Genetics, DeKalb, Ill.

[21] Appl. No.: 827,025

[22] Filed: Jan. 24, 1992

[51] Int. Cl.[6] ............... A01H 5/00; A01H 4/00; C12N 5/04
[52] U.S. Cl. ................. 800/200; 800/250; 800/DIG. 56; 435/240.4
[58] Field of Search ............ 800/200, 250, DIG. 56; 435/240.4, 45.49; 47/58.03, 58.05

[56] References Cited

U.S. PATENT DOCUMENTS

| | | |
|---|---|---|
| 3,903,645 | 9/1975 | Bradner . |
| 4,368,592 | 1/1983 | Welch . |
| 4,517,763 | 6/1985 | Beversdorf et al. . |
| 4,581,847 | 4/1986 | Hibberd et al. . |
| 4,594,810 | 6/1986 | Troyer . |
| 4,607,453 | 8/1986 | Troyer . |
| 4,626,610 | 12/1986 | Sun . |
| 4,627,192 | 12/1986 | Fick . |
| 4,629,819 | 12/1986 | Lindsey . |
| 4,642,411 | 2/1987 | Hibberd et al. . |
| 4,654,465 | 3/1987 | Lindsey . |
| 4,658,084 | 4/1987 | Beversdorf et al. . |
| 4,658,085 | 4/1987 | Beversdorf et al. . |
| 4,677,246 | 6/1987 | Armond et al. . |
| 4,686,319 | 8/1987 | Shifriss . |
| 4,731,499 | 4/1988 | Puskaric et al. . |
| 4,737,596 | 4/1988 | Seifert et al. . |
| 4,751,347 | 6/1988 | Erickson . |
| 4,767,888 | 8/1988 | Ayotte et al. . |

FOREIGN PATENT DOCUMENTS

0270356 2/1987 European Pat. Off. .

OTHER PUBLICATIONS

Soss (1987) "Morphology" Jn. Corn & Corn Improvement. ASA Publications pp. 89–110.
Meglyi (1984) Crop Science vol 24, pp. 545–549.
Smith et al. (1992) "Fingerprinting Crop Varieties" Jn Advances in Agrinomy vol 47, pp. 85–140.
Gordon-Karn et al. (1990) The Plant Cell vol. 2 pp. 603–618.
Chandler et al., "Two Regulatory Genes of the Maize Anthocyanin Pathway Are Homologous: Isolation of B Utilizing R Genomic Sequences," The Plant Cell, 1:1175–1183 (1989).
Culotta, "How Many Genes Had to Change to Produce Corn," Science, 252:1792–1793 (1991).
Duvick, "Genetic Contributions to Yield Gains of U.S. Hybrid Maize, 1930 to 1980," In Genetic Contributions to Yield Gains of Five Major Crop Plants: Proceedings of a Symposium sponsored by Div. C–1, Crop Science Society of America, Dec. 2, 1981 in Atlanta, Ga.; W. R. Fehr, pp. 15–47, published by Crop Science Society of America and American Society of Agronomy, Madison, Wis.
Green & Rhodes, "Plant Regneration in Tissue cultures of Maize," In Maize for Biological Research, ed. W. F. Sheridan, A Special Publication of the Plant Molecular Biology Assoc, pp. 367–372 (1982).
Hauptmann et al., "Evaluation of Selectable Markers for Obtaining Stable Transformants in the Gramineae," Plant Physiol., 86:602–606 (1988).
Larson & Hanway, "Corn Production," In Corn and Corn Improvement, ed. G. F. Sprague, No. 18 in Agronomy Series, pp. 625–669 (1977) published by American Society of Agronomy, Inc. in Madison, Wis.
Ludwig et al., "A Regulatory Gene as a Novel Visible Marker for Maize Transformation," Sicence, 247:449–450 (1990).
Poehlman, In Breeding Field Crops, 3rd ed., AVI Publishing Company, pp. 469–481 (1987) published in Westport, Conn.
Sprague & Eberhart, "Corn Breeding," In Corn and Corn Improvement, ed. G. F. Sprague, No. 18 in Agronomy Series, pp. 305, 320–323 (1977) published by American Society of Agronomy, Inc. in Madison, Wis.
Troyer, "A Retrospective View of Corn Genetic Resources," Journal of Heredity, 81:17–24 (1990).
Withers & King, "Proline: A Novel Cryoprotectant for the Freeze Preservation of cultured Cells of Zea mays L.," Plant Physiol., 64:675–678 (1979).

*Primary Examiner*—Gary Benzion

DK 554 PEST PROFILE

*Attorney, Agent, or Firm*—Arnold, White & Durkee

[57] ABSTRACT

This invention relates generally to the production of maize, commonly known in the United States as corn, and more specifically to hybrid corn plants with certain advantageous phenotypes resulting from interactions of the haploid genetic contributions of inbred parental lines. This invention relates to the hybrid genetic complement, the expression of which produces these phenotypes and to the complement as housed in seeds and tissues, in particular, those capable of producing or regenerating the hybrid plants either in vivo or in vitro. An aspect of this invention, hybrid DK554, is characterized by many advantageous phenotypic traits including superior yield, staygreen, and roots. It has characteristic restriction fragment length polymorphism (RFLP) and isozyme profiles.

4 Claims, 2 Drawing Sheets

RELATIVE MATURITY MAP

METHODS AND COMPOSITIONS OF A HYBRID GENETIC CORN COMPLEMENT, DK554

BACKGROUND OF THE INVENTION

1. Field of the Invention

This invention relates generally to the production of maize, and more specifically to hybrid corn plants with certain advantageous phenotypes resulting from interactions of the haploid genetic contributions of inbred parental lines. Seeds and tissues, in particular, those capable of producing or regenerating the hybrid plants either in vivo or in vitro are disclosed. An aspect of this invention, hybrid DK554, is characterized by many advantageous phenotypic traits including exceptional yield to moisture ratios, staygreen and root strength. It has characteristic restriction fragment length polymorphism (RFLP) and isozyme profiles.

2. Description of the Related Art

Crop improvement has been a major focus of human agriculturists since the hunting gathering societies moved into the agricultural phase of human existence. Early crude attempts to improve crops focused on the choice of parental plants to become the progenitors of the next generation, a choice made on the readily detectable characteristics of the parents. The objective was to produce offspring having the advantageous traits of the parents. However, from what we now know of genetics and genetic theory, such efforts were usually doomed to failure—in some instances because the parental phenotypes could not be reconstructed in their offspring due to disruption of the genetic complements of the parents by segregation of a diploid complement into haploid gametes, and shuffling of the genetic material by recombination. Even worse, certain combinations of parental genomes yielded deleterious effects due to interactions of genes at the same or different loci. As a consequence, success at crop improvement was painstakingly slow, sporadic and rarely reproducible.

Modern sophisticated crop breeding of the 1900's has benefitted from knowledge gained by Gregor Mendel and others in the late 1800's indicating that both single gene (mendelian) and polygenic control must be considered when planning breeding programs to improve crop characteristics. In fact, all corn as we know it today, *Zea mays*, is a result of human manipulation. It is not a plant occurring sporadically in nature.

Despite much knowledge that has developed subsequently, each breeding program represents at least in part a new attempt to mold the plant germplasm into new and more productive, more desirable genotypes. This molding process benefits from the development over many years of inbred lines. These lines are not found in the wild, that is, in natural settings, and by themselves are generally not commercially productive. However, inbred lines are valuable as repositories for genes that are preserved in relatively stable conditions due to the true-breeding capabilities of these genetically uniform lines. Such genes are then available to be repeatedly tested for their effects in various breeding combinations and to be incorporated into commercially desirable crops.

Inbred lines are those that are essentially homozygous. Initial repeated inbreeding concentrates a subset of ancestral genes in offspring. Lines may also be improved in this fashion. The more genetically similar the ancestral lines, the more rapid the approach to homozygosity. Self-fertilization is a way of maintaining homozygosity. Homozygosity refers to the condition of the genetic complement in which the paired diploid positions at each locus are occupied by identical alleles. Alleles are conditions of a gene which differ in their nucleotide sequences. Alleles are recognizable when they are expressed as distinct phenotypes. Homozygosity in an inbred line is achieved by repeated inbreeding. In general, by the sixth or seventh generation, the inbred line is considered genetically pure, or "true-breeding" although spontaneous changes in the genetic material (mutations) and other events may preclude absolute homozygosity. Environmental variations may produce some phenotypic variability even within genetically identically lines.

Unfortunately, reduction in yield performance and the appearance of other plant characteristics which are undesirable characteristically accompanies inbreeding. In addition, progressive selfing (self-fertilization) of inbred lines reduces plant vigor. Many of these deleterious effects are caused by homozygosity for deleterious recessive genes whose effects are unmasked by loss of desirable dominant alleles. Consequently, inbred corn lines per se are not grown to be used as commercial crops. However, they are extremely important as vehicles to preserve genes and to produce first generation ($F_1$) hybrids by the process of hybridization by crossbreeding.

Hybrid plants are likely to be heterozygous at many loci, as opposed to being homozygous, in contrast to the inbred parental lines. Heterozygosity refers to the fact that at a locus, there are different conditions of a gene (different alleles). One desirable result of crossing two inbred lines is that hybrid vigor or heterosis may arise wherein the hybrid plants produced have markedly improved yields, better stalks, better roots, better uniformity and better insect and disease resistance, than either inbred parent. For corn used as animal feed, one of the goals is decreasing the amount of feed needed for animal weight gain.

Furthermore, as result of self-pollination of these $F_1$ hybrid plants, a process possible in plants such as corn which have both male and female sex organs on the same plant, or of cross-pollination of $F_1$ hybrid plants, a second generation ($S_1$ or $F_2$) hybrid may be produced. Non-parental genetic combinations occur in these offspring due to independent assortment at meiosis of genes on different chromosomes and by recombination of genes on homologous (matched and paired at meiosis) chromosomes. Because of this further shuffling of the genetic material from the $F_1$ into the $F_2$, some of the $F_2$ hybrid plants produce less desirable plants than those of the $F_1$ in terms of the traits discussed above, due to homozygosity for deleterious recessive alleles and other disruption of the $F_1$ genetic complement. In addition, there is increased variability overall of trait performance in the $F_2$ due to this extensive genetic shuffling, in particular, if many loci are involved in controlling a particular trait. It is not generally beneficial, therefore, for farmers to save the seed of $F_1$ hybrids. Rather, a cycle of purchase by farmers each year of $F_1$ hybrid seed for planting is the rule. Corn breeders attempt to market new improved seed each season to attract these consumers.

North American farmers plant over 70 million acres of corn at the present time. There are extensive national and international programs in commercial corn breeding. Clearly this endeavor has a major impact on humanity in the form of food production. Basic methods of cross breeding inbred lines to produce hybrids are known in concept by those skilled in the art. However, actual manipulation of these basic methods to generate improved hybrids is a delicate, arduous and sophisticated process. Breeders armed with methods to physically control plant breeding, and with an array of inbred lines with various known phenotypic traits, cannot expect to merely go into the field with these inbred lines, breed them using well-established general methods, and walk out of their laboratories, greenhouses and fields with superior hybrids.

One of the first difficulties encountered is in breeding superior inbred parental lines, due to the difficulties discussed above which are inherent in inbreeding, for example, reduced vigor.

The skilled corn breeder also must make determinations regarding which combinations of these inbred lines should be selected to produce improved hybrids. The traits selected for commercial desirability are generally not expressions of genes operating in a vacuum. Rather, to produce a plant which as a whole has an array of desirable characteristics, there must be a balance in terms of improvements. Phenotypic traits may show positive or negative correlations within inbred lines and between those lines and their hybrid progeny. Consequently, improving one trait may lead to poor outcome of another. Furthermore, hybrid plants that are beneficial in one set of environmental conditions may do poorly in others.

With the desperate need for increased food production within diverse areas of the world, and for growing various crops in different locations of the world for maximum input and control of local persons over their agricultural destiny, it is important to develop wide ranges of hybrids that are going to perform well in both specific and general ecological and commercial niches.

Evidence of the difficulties inherent in commercial crop breeding is provided by the continual and highly competitive research in both the laboratory and the field revolving around improvement of inbred and hybrid lines. Removal of some of the uncertainty in large scale and expensive field testing is resulting from the application of methods of molecular biology whereby segments of the genetic complement may be singled out for faster, more selective and more successful breeding, and genetic complements may be combined in vitro, that is, in laboratory tissue culture vessels rather than in corn fields.

Some of the phenotypic traits for which improvements have continually been sought by hybridization of corn, include yield; stalks; roots; resistance to insecticides, pests and disease; and markedly more uniform characteristics. With mechanical harvesting of many crops, uniformity of plant characteristics such as germination and stand establishment, growth rate, maturity, and fruit size, is important. Other desirable phenotypic characteristics for field crops include tolerance to heat and drought, reduced time to crop maturity, and better agronomic quality. However, despite some successes in breeding programs in the 1900's, progress is painstakingly slow—each qualitative improvement representing a small quantitative step.

Currently, it appears as if there is polygenic control over most commercially desirable traits such as yield. This means that many genes, generally on many chromosomes, contribute to the phenotypic appearance of the plant. The variance of the trait in inbred lines is less than that expected in hybrids formed from inbreds because of intralocus and interlocus interactions in hybrids. Consequently, selective breeding programs to improve crops are not completely predictable.

SUMMARY OF THE INVENTION

Corn is the most important crop in the United States (Duvick, 1984). Consequently, a great deal of effort is expended to increase corn production and improve quality. A major method to achieve these goals is to produce hybrid plants which are superior to their inbred parents.

This invention addresses some of the shortcomings in the prior art of corn hybridization, and discloses a corn hybrid genetic complement that, when expressed in the form of a corn plant, exhibits superior characteristics that include exceptional yield to moisture ratios, staygreen and root strength. This unique combination of phenotypic traits is evident by comparison with other commercially valuable hybrids of similar maturity, none of which have been found to exceed the combined performance of DK554 for yield and staygreen. Yield is a trait of major commercial interest because it measures grain output per acre. Staygreen is a measure of general health of the plant. Root strength is measured by "root lodging," the percent of plants leaning at greater than 30° angle to the ground. A low number is preferable.

"Genetic complement" refers to that aggregate of nucleotide sequences that, when expressed in corn cells, yields a phenotype in corn plants, or components of plants including cultured cells, which includes phenotypic traits within specified quality and quantity ranges. As an example of a phenotypic trait of DK554, the improved yield of the hybrid of this invention compared to 3 commercially successful hybrids of similar maturity is dramatic, from between 6.1 to 6.7 bushels per acre in FACT trials (described herein). This is to be contrasted with the increase in U.S. corn yield of about 2 bushels per acre in recent times reported by Troyer (1990), an improvement equated by Troyer to a value of about $330 million per year for the U.S.

A method used to produce the hybrid genetic complement of the present invention was to combine the genetic complements of two different inbred lines. These lines were produced by repeated planned crossing of ancestrally related corn plants to concentrate certain genes within the inbred lines.

More specifically, the hybrid genetic complement of the present invention was produced by interbreeding two corn lines which differ in their allelic constitutions at least at some loci. Alleles are conditions of genes that generally occupy the same locus, or position on a chromosome. Genes are sequences of nucleic acids, more specifically, DNA. Different alleles are characterized by different sequences of the DNA. These sequences are still capable of occurring at the same locus, although because of their sequence variation, they may be transcribed as different mRNA nucleic acid sequences. Depending on the coding equivalency of the altered sequences, there may be changes in the translation into amino acid sequences in the gene products.

In an illustrative embodiment, the parental complements were contributed to the hybrid of this invention by transmission as haploid complements, that is, in the form of gametes, each gamete comprising one member of the pair of alleles at each locus. More particularly, this invention relates to a hybrid genetic complement formed by the combination of a haploid genetic complement from each of the inbred lines of corn designated respectively, FBLL and LIBC4. The hybrid complement is designated DK554.

Because the parents are members of inbred lines, all haploid complements derived from the parent are expected to be essentially the same genetically, with the exception of, for example, mutations and the presence of heterozygous loci if there was not 100% homozygosity. Although the genetic complements of the inbred parental lines will be generally the same as that contained in haploid pollen or eggs derived from plants of the line, there may be some effects on offspring of maternal cytoplasmic factors. In addition, one of the parental lines may be preferred as the male and the other as the female due to phenotypic characteristics of the parental plant that affect reproduction. For example, one of the lines may have higher seed yield, one may shed pollen better, one may have preferred seed or tassel characteristics.

In embodiments wherein the hybrid genetic complement is produced by field breeding schemes or by another method wherein gametes designated as pollen or egg are combined, the preferred source for the maternal haploid complement is FBLL and for the paternal haploid complement LIBC4. LIBC4 is preferred as a paternal rather than maternal source because of poor seed quality from this line.

Because the inbred lines by definition are homozygous at most loci, the resulting hybrid is likely to be heterozygous at most loci unless the parental lines had the same allelic complement at some loci, perhaps due to common ancestry. The goal of this invention was to produce heterosis, a phenomenon wherein the heterozygote produces a phenotype that is more desirable than that exhibited by either parent. In the hybrid genetic complement disclosed herein, that goal has been achieved.

Figure 1:
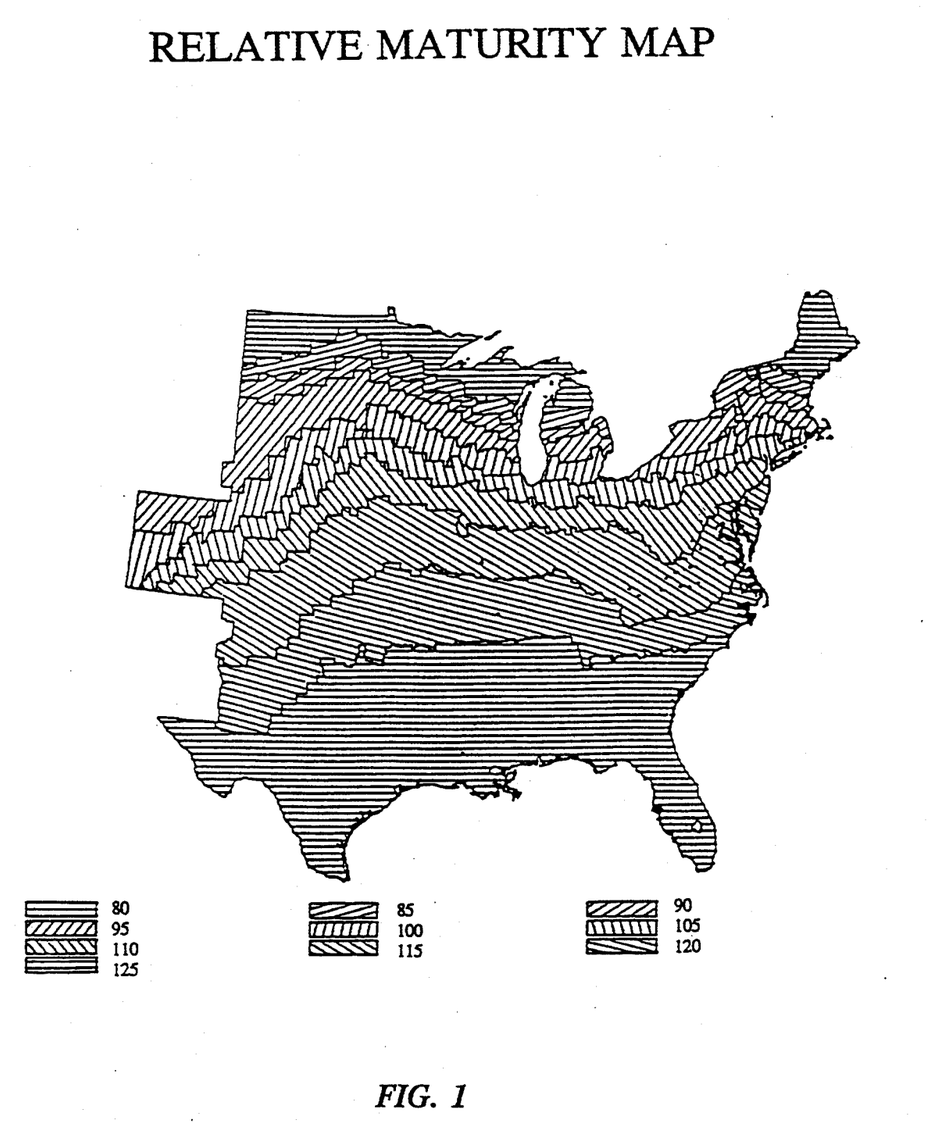
FIG. 1 is a relative maturity map used to define temperature ranges for corn plant growth.

The complement designated DK554 when expressed as a plant or its components thereof, has superior advantages when compared to other hybrid competitors of similar maturity. Maturity is a concept well known to those skilled in the art and refers to the observation that plants of different genotypes take different times to mature. This period must fit the temperature range of the environment in which the plants are raised to permit reproduction (FIG. 1). In other words, if a plant does not mature before the temperature drops below a permissible level, the plant can not be successful.

The hybrid corn plant designated DK554 typically has a relative maturity of about 104 days. (FIG. 1) It is characterized by exceptional yield for its maturity, staygreen, and root strength. Based on overall FACT data, DK554 is an exceptionally high yielding hybrid. FACT is an acronym for Field Analysis Comparison Trials (strip trials), on-farm testing programs to perform final evaluations of the commercial potential of a product. This is primarily a function of its high yield to moisture ratio.

A very distinctive feature of DK554 is that its high yield to moisture ratio is combined with above average staygreen. No hybrid with which it has been compared in FACT shows better staygreen at the same harvest moisture in research data collected by Applicants. The staygreen of DK554 traces in part to the late season health of its root system. This hybrid exhibits average resistance to most foliar diseases. It typically produces significantly higher yields, 6.1 to 6.7 bushels per acre, based on FACT trials. These performance and comparison trials are performed on actual farms under conditions which approximate the actual growing conditions used by farmers who will eventually purchase the seeds of the hybrid. These are "real life" trials to follow up and support research testing. Research testing is a more vigorous evaluation of basic characteristics of hybrids on smaller plots of land.

Figure 2:
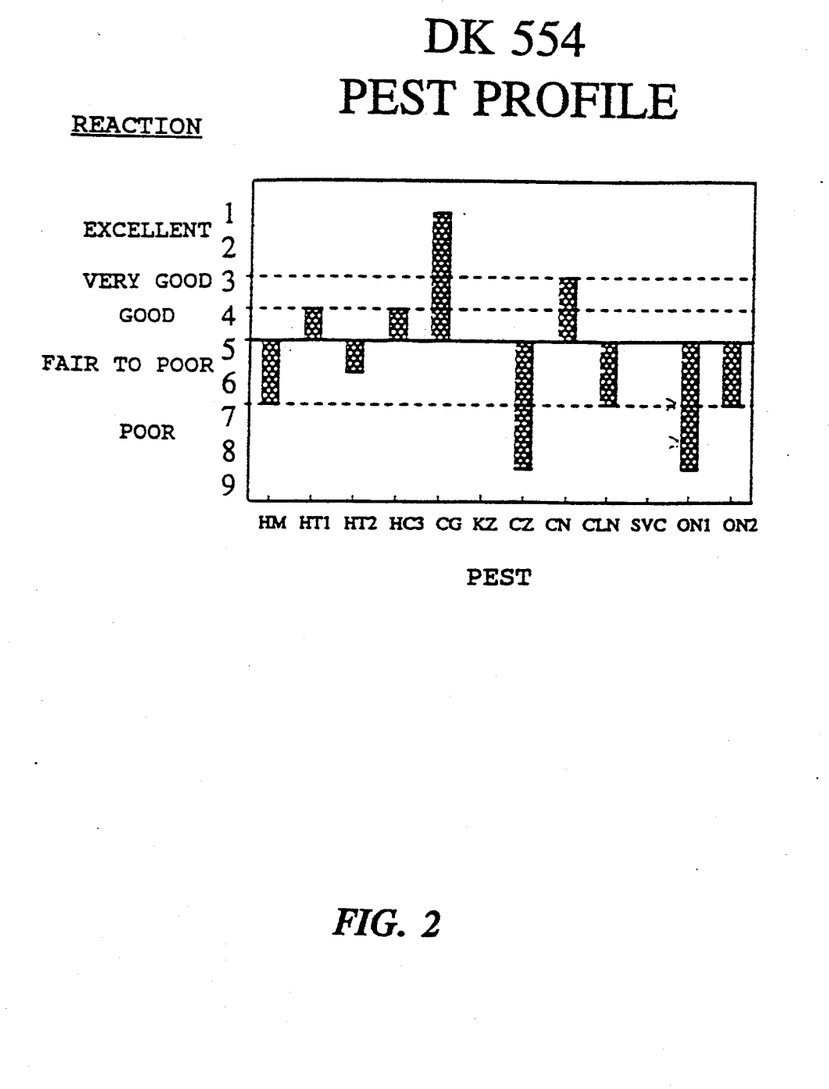
FIG. 2 is a graphical presentation of the reaction of DK554 to disease and insects. The following abbreviations appear on the graph.

Other favorable phenotypic characteristics of DK554 comprise staygreen and root strength. (see Appendix for definitions of these traits). FIG. 2 and Tables 2-4 list identifying features and characteristics of these hybrids. Table 1 compares their performance with other commercially successful hybrids. It is unexpected to improve several desirable traits at once by breeding. "Gains may be made in the defensive traits but not in yield, or new hybrids may be improved in yield but not in defensive traits." (Duvick, 1984, p. 47).

For methods of combining the FBLL and LIBC4 genetic complements other than breeding in fields or greenhouses for example, in vitro combinations performed in tissue culture, there need be no preferred maternal or paternal designation. Moreover, the genetic complements combined in vitro may represent only the subset of genes necessary to produce the superior phenotype of DK554. These nucleic acid segments may be determined by mapping of quantitative loci using discrete markers e.g., by the QTL method, (See Asins (1988); Beckmann and Soller (1983); Burr et al. (1983); Lande and Thompson, (1990); Lander and Botstein (1989); Paterson et al., (1988); EP 0 306 139 A2; PCT/US89/00709). Nucleic acid segments that have no commercially necessary coding function, need not be included.

The hybrid genetic complement designated DK554 exists in all somatic (non-germinal) cells of a corn plant, and is claimed in all those aspects, in particular, roots, stems, leaves, seeds and all flowering parts, including pollen grains. All these parts of plants derived from the hybrid DK554 are claimed because all have the novel genetic complement of this invention.

The pollen grains are haploid samples of the diploid genetic complement of the hybrid. These haploid samples result from independent segregation of the individual maize chromosomes and shuffling of the genes on homologous chromosomes by the natural recurring phenomenon of recombination at meiosis.

The hybrid genetic complement may be produced in several ways, either in vivo or in vitro. The following in vivo method comprises a breeding scheme which may be used to produce a hybrid corn plant in the field:

(a) planting in pollinating proximity seeds from inbred corn lines having the designations, FBLL (ATCC Accession No. 75748) and LIBC4 (ATCC Accession No. 75747);

(b) cultivating corn plants resulting from the planting before the time of flowering;

(c) emasculating the plants of inbred corn line FBLL;

(d) allowing cross-pollination to occur between said corn lines; and (e) harvesting seeds produced by the plants of the emasculated corn plants from the line designated FBLL.

Hybrid plants may be grown from seeds with the genetic complement disclosed herein by methods well known to those skilled in the art. These seeds have been deposited with the ATCC as Accession No. 75748.

This invention also relates to the hybrid genetic complement contained in seeds. Plants grown from these seeds by methods well known to those skilled in the art are expected to exhibit the characteristics listed in Tables 1 through 4 and FIG. 2.

To produce the hybrid genetic complement in vitro, a plant may be regenerated from cells in culture (Gordon-Kamm, et al., 1990). To regenerate hybrid plants, cells are obtained which comprise the hybrid genetic complement, for example, somatic cells from a DK554 corn plant. These cells are then cultured in vitro in a media comprising an embryogenic promoting hormone until callus organization is observed. At this point, cells are transferred to media which includes a tissue organization promoting hormone. After tissue organization is observed, the cells are subcultured onto media without said hormone, to allow for shoot elongation or root development. Finally, the plantlets are transferred onto a minimal medium to provide for hardening of the plant.

Embodiments of the embryogenic promoting medium are dicamba, 2,4-D and the like. Embodiments of the tissue organization promoting medium comprises BAP (6-benzyl-aminopurine), myoinositol, 2,4-dichlorophenoxyacetic acid, ABA (abscisic acid), NAA naphthol acetic acid), IAA (indole acetic acid) and 2IP (2-iminopurine). IBA may be used to stimulate rooting. Minimal media comprises Clark's media.

The combination of genetic complements of the inbred lines FBLL and LIBC4 to yield the hybrid complement disclosed herein is claimed within the scope of this invention regardless of the method used to produce it.

A deposit of 2500 seeds each of inbred plants designated FBLL and LIBC4 was made with the American Type Culture Collection, Rockville Pike, Bethesda, Md. on Apr. 18, 1994. These deposited seeds have been designated, for public accession purposes, as 75748 for FBLL, and 75747 for LIBC4. These deposits were made in accordance with the terms and provisions of the Budapest treaty relating to deposit of microorganisms.

The deposits are made for a term of at least thirty years and at least five years after the most recent request for the furnishing of a sample of the deposits was received by the depository. Prior to making those deposits, Applicants state that seeds of inbred corn plants FBLL and LIBC4 are on deposit at DeKalb Genetics Corporation, Sycamore, Ill., and that such seeds are accessible and available to the Commissioner of Patents and Trademarks during pendency of this application.

Phenotypic traits characteristic of the expression of the hybrid genetic complement of this invention include those that are distinguishable by electrophoretic separation of DNA sequences cleaved by various restriction endonucleases. These traits (genetic markers) are termed RFLP (restriction fragment length polymorphisms).

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., the bacteria E. coli. Variations in RFLP's result from nucleotide base pair differences which alter the cleavage sites of the restriction endonucleases, yielding different sized fragments.

Restriction fragment length polymorphism analysis was conducted by Native Plants Incorporated (NPI) (Table 3). This service is available to the public on a contractual basis from Linkage Genetics (Table 3). For this analysis, the genetic marker profile of the parental inbred lines were determined. Because these inbreds are essentially homozygous at all relevant loci, they should have only one allele at each locus. Consequently, the diploid genetic marker profile of the hybrid offspring of the inbred parents should be the sum of those parents, e.g., if one parent had the allele A at a particular locus, and the other parent had B, the hybrid AB is by inference. The RFLP complement is presented in Table 3.

Probes were prepared to the fragment sequences, these probes being complementary to the sequences thereby being capable of hybridizing to them under appropriate conditions well known to those skilled in the art. These probes are labelled with radioactive isotopes or fluorescent dyes for ease of detection. After the fragments are separated by size, they were identified by the probes. Hybridization with a unique cloned sequence permits the identification of a specific chromosomal region (locus). Because all alleles at a locus are detectable, RFLP's are codominant alleles, thereby satisfying a criteria for a genetic marker. They differ from some other types of markers, e.g, from isozymes, in that they reflect the primary DNA sequence, they are not products of transcription or translation. Furthermore, different RFLP profiles result from different arrays of restriction endonucleases.

Other characteristic phenotypic traits include the isozyme variants listed in Table 4. These are codominant genetic markers that delineate segments of nucleic acids characterizing the genetic complement.

DEFINITIONS

Cross-pollination
pollen from a flower of one plant is used to fertilize a different maternal plant.

Elite Germplasm
in its area of adaptation, germplasm that is considered by breeders to possess a high level of favorable traits.

Substantially Similar Genetic Complements
genetic complements having nucleic acid sequences which code for the same exons, or mutant or variant sequences which either are codon equivalents of the exons or do not detectably affect the phenotype as disclosed herein as it is generally detected.

Plant Components
all somatic cells, including protoplasts, calli, and parts of plants, from which plants can be regenerated in tissue culture, e.g., flowers, kernels, ears, cobs, leaves, husks, and stalks.

Self-pollination
pollen from one flower is transferred to the same or another flower of the same plant.

BRIEF DESCRIPTION OF THE DRAWINGS

Other objects and advantages of the invention will become apparent upon reading the following detailed description and upon reference to the drawings in which.

| Code | Description |
|---|---|
| | Foliar Diseases (Fungal) |
| HM - | *Heliminthosporium maydis* (Syn. = *Bipolaris maydis*) race 0, which causes southern corn leaf blight. |
| HT1 & HT2 - | *Helminthosporium turcicum* (Syn. = *Exserohilum turcicum*) races 1 and 2, which cause northern corn leaf blight. |
| HC3 - | *Helminthosporium carbonum* (Syn. = *Bipolaris zeicola*) race 3, which causes Helminthosporium leaf spot. |
| CG - | *Colletortrichum graminicola*, which causes the foliar phase of anthracnose. |
| KZ - | *Kabatiella zeae*, which causes eyespot of corn. |
| CZ - | *Cercospora zeae-maydis*, which causes gray leaf spot of corn. |
| | Systematic Disease (Viral) |
| CN - | *Corynebacterium nebraskense* (Syn. = *Clavibacter michiganense* subsp. nebraskense), which causes Goss' disease |
| CLN - | Corn Lethan Necrosis (combination of Maize Chlorotic Mottle V irus and Maize Dwarf Mosaic Virus). |
| SVC - | Southeastern Virus Complex (combination of Maize Chlorotic Dwarf Virus and Maize Dwarf Mosaic Virus). |
| | Insects |
| ON1 - | *Ostrinia nubilalis*, first brood of European corn borer. |
| ON2 - | *Ostrinia nubilalis*, second brood of European corn borer. |

DESCRIPTION OF THE PREFERRED EMBODIMENT

This invention relates to a hybrid genetic complement produced by combining the haploid genetic complements of two parental inbred lines of corn.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred line, all loci are homozygous. Because many loci when homozygous are deleterious to the plant, in particular leading to reduced vigor, production of inbred lines is an unpredictable and arduous process. Under some conditions, heterozygous advantage at some loci effectively bars perpetuation of homozygosity.

Inbreeding requires coddling and sophisticated manipulation by human breeders. Even in the extremely unlikely event inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred lines is to have a known reservoir of genes whose gametic transmission is at least somewhat predictable. The development of inbred lines generally requires at least about 5 to 7 generations of selfing. Inbred lines are then cross-bred in an attempt to develop improved $F_1$ hybrids.

The development of corn hybrids to generate crops with improvements in commercially desirable traits, is a sequential and laborious process of recurrent selection of inbred or partially inbred lines to form breeding pools from which new lines are further selected either by self-pollination and selection of desired phenotypes, and further inbreeding. Inbreds are then selected to be crossed with other inbreds to form hybrids which are evaluated in terms of their commercial potential. Many generations of breeding are involved before final selections are made of desirable hybrids for commercial use. "Uncommonly great genetic variability is present in and among the diverse lines, varieties, and races of corn in the world." (Coe et al., 1988, p. 111.) A breeders task is to delve into the morass of genetic variability and extract a new, improved combination of genes.

Herculean efforts have been undertaken, particularly in the 1900's by commercial seed producers in continuous research and development directed toward crop improvement. Selection and development of inbred lines is tenuous and tedious. Challenges posed by varying climates, new pests, and economic trends, prevent successful selection of "off the shelf" inbred lines to get a hybrid with desired traits. Troyer (1990), chronicles the excruciatingly tedious, complex venture of corn breeding for crop improvement. Although there are some well-established corn breeding techniques, they are not cook-book protocols which can be implemented without significant human interaction. Moreover, they are guidelines for improvement, not blueprints for success.

Sprague and Eberhart (1977) illustrate the complexity of the involvement of the human breeder in corn programs. More importantly, this reference discusses the relevance of additive and non-additive genetic effects. In additive effects, the genes contributed to an offspring by a certain line produce characteristic effects, usually regardless of the order of pairing, when combined with genetically analogous germplasm. Non-additive effects, however, must be considered in predicting phenotypic effects resulting from crossing certain genotypes. Dominance (intra-locus genetic interactions) and epistasis (inter-locus effects) are not completely predictable functions of the simple combinations of parental traits.

It is not expected that a parental line with superior traits will convey these traits to offspring of a cross with another parental line. Transmission of traits depends on the nature of the genetic transmission and the basis for the phenotypic trait. Those traits due to recessive inheritance in either parent, are expected to disappear or be modified in a hybrid because the homozygosity underlying the trait is disrupted unless identical alleles are donated from each parent to the relevant loci in the hybrid. The goal is that the disruption is beneficial, that is, heterosis results. For any one cross that turns out to be superior, many, many such crosses will likely fail. Interactions among loci (epistasis) are also generally unpredictable in offspring of new genetic parental combinations.

The performance of an inbred line is judged by its performance when crossed with other inbred lines to produce hybrids.

The general combining ability of a particular inbred is determined by its average performance in a series of hybrid combinations. General combining ability is said to measure mainly additive genetic effects. Specific combining ability (sca) refers to the performance of two particular inbreds in a specific cross. Specific combining ability measures nonadditive types of gene interactions.

One of the traits for which hybridization has been employed to cause improvement is yield per acre of corn. For example, in the Apr. 17, 1974 edition of the Wall Street Journal, an article entitled "In Search of Superbean," it was pointed out that soybeans could not easily be hybridized and therefore fell far behind corn and productivity increased. During the period of 1950 to 1973, soybeans increased in productivity from 21.8 to 27.8 bushels per acre, whereas corn increased from 38.4 to 91.4 bushels per acre. Improvements since that time have been sought by sophisticated plant and genetic manipulation.

Whether two particular inbreds combine to produce a high-yielding single cross depends upon the extent to which favorable genes for yield from one inbred supplement those contributed by the second inbred. Mixing parental germplasm from inbred lines in the cauldron of the $F_1$ hybrid does not lead to a completely predictable spectrum of traits in that hybrid. This is because traits in the hybrid result from interactions among genes at the same locus (dominance, overdominance), genes at different loci (epistasis) and genes and environments. The meiotic shuffling of the genes plus the interaction of genes with the environment will lead to any particular trait. It is the traits which are sought as commercially desirable.

Hybrids may be produced from single or multiple parental inbred line crosses, although of course only two parents may be used to produce any particular plant. However, successive single cross hybrids from different inbred lines will lead to the merging of the genetic parental complements of various inbred lines into one hybrid. It is this matrix of multiple merging that illustrates the sophisticated methods of selection and crop improvement.

Complex mathematical models have been developed to predict offspring phenotypes based on parental genotypes and the environment (Falconer, 1960; Sprague and Eberhart, 1977).

Breeding Methods to Develop the Hybrid Genetic Complement of the Present Invention The two inbred parental lines FBLL and LIBC4 were crossed to produce the hybrid DK554. Based on well-established genetic principles, it is known that a homozygous line crossed to another homozygous line is expected to yield hybrids, usually designated $F_1$, that are genotypically the same barring rare events such as mutation. Of course, the phenotype of the hybrid lines may not always be identical when the same inbred lines are used as parents because the comparability of the phenotypic expression of the genotype depends on the similarity of the environmental conditions interacting with the genotype to produce the phenotype. In general, the phenotypes are expected to be similar unless the phenotype or aspects thereof is strongly dependent on environmental conditions.

Reciprocal crosses refer to interchange of the sex of the parents. For many crosses, the outcome is the same regardless of the assigned sex of the parental lines. However, there is often one of the parental lines that is preferred as the maternal line because of increased seed yield and production characteristics. Some lines produce tighter ear husks leading to more loss, for example due to ear rot. There may be delays in silk formation which deleteriously affect timing of the reproductive cycle for a pair of parental inbreds. Seed coat characteristics may be preferable in one line. Pollen may be shed better by one line. Other variables may also affect preferred sexual assignment of a particular cross. Although either parent may serve as the maternal or paternal plant, in the production of DK554, LIBC4 is preferred as the male, FBLL as the female parent because it has poor pollen shed.

Because there is no adequately reliable way to predict the overall phenotype of any particular $F_1$ hybrid, tens of thousands of hybrids resulting from large numbers of crosses are required and must be evaluated each year. These hybrids are then screened and evaluated in small scale field trials ("R" or research trials, Table 1). Typically, about 10–15 phenotypic traits are measured. These traits are selected for their potential commercial value. A selection index of the most commercially important traits is used to help evaluate hybrids. For DK554, yield, moisture, percent dropped ears, percent stalks lodged and percent root lodged were used in the selection index.

After one year of evaluation, approximately 95% of the hybrids are rejected on the basis of their performance not being above that of previously developed hybrids.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. FACT, an acronym for Field Analysis Comparison Trial (strip trials), is an on-farm testing program employed by DeKalb Plant Genetics to perform the final evaluation of the commercial potential of a product. (See Table 1 for DK554 results as compared with some competitors.) That is, comparisons of the new hybrids were made to competitive hybrids in order to determine if there was any advantage to further commercial development of the new hybrids. Comparisons were made to hybrids of similar or identical maturity.

Time to maturity is an important characteristic for a corn line and must match the environment in which the corn is to be planted. If there is only enough heat accumulated to mature a hybrid corn plant in 80 days, and the plant requires 125 days, there will not be time enough to enter a reproductive phase. Maturity of a hybrid is not completely predictable from that of the parental inbreds. Another complication is that the range of maturity will be based on the selection environments.

Strip trials compare the phenotypes of hybrids grown in as many environments as possible. Strip tests were performed in many environments to assess overall performance of the new hybrids and to select optimum growing conditions. The corn being compared is of similar maturity. The corn is grown in close proximity, consequently, environmental factors that affect gene expression are minimized. These factors include moisture, temperature, sunlight and pests.

For a decision to be made that a hybrid is worth making commercially available, it is not necessary that the hybrid be better than all other hybrids. Rather, significant improvements must be shown in at least some traits that would create improvements in some niches, in particular in what is seen as the target market.

DK554 was found to be an unexpectedly superior hybrid. Results of experiments designed to test the response of DK554 to insects and resistance to disease, are shown in FIG. 2. The levels of disease and insect resistance make DK554 a highly acceptable hybrid in its marketplace. It is unexpected to improve several traits at once in the same hybrid. "Gains may be made in the defensive traits but not in yield, or new hybrids may be improved in yield but not in defensive traits." (Duvick, 1984, p. 47).

Table 1 presents examples of comparisons of performance data for DK554 versus three hybrids of commercial value selected because of similar maturity and potential competition in the marketplace. These data represent results across years and locations for strip trials.

The "NTEST" represents the number of paired observations in designated tests at locations around the United States.

As can be seen in Table 1, DK554 has significantly higher yield when compared to three commercially successful hybrids designated DK535, DK547 and PION3475. The increased yield in bushels per acre is 6.1 to 6.7 in FACT trials. Significant improvements are also shown in Table 2 for many other traits, notably yield to moisture ratio, staygreen and root strength. Staygreen is a scale 1–9 (9=best) of general health of the plant after the ear leaves have reached maturity. Root lodging is a measure of standability. Root lodging is the percent of plants leaning at greater than a 30° angle to the ground, a measure of root strength.

Therefore, root strength is commercially valuable. Root strength exhibited by DK554 is of particular value. Commercial hybrid maize generally grows from about 7–9 feet tall with each plant having either one or two ears. The ear normally grows about one third the way up the plant or about 2½ to 3½ feet from the ground. Consequently, the maize plant, while providing a large ear has a substantial leaf and stalk structure and a considerable mechanical stability problem in that the heavy ear is about 3 feet from the ground with 6 feet of stalk and tassels extending above that. In the past, efforts have been made to develop strong stalk and branching of the secondary roots in maize to help alleviate the stability problem. While these efforts have improved the mechanical stability of maize considerably, heavy windstorms and rain can still wreck havoc in a field of maize. That is why the root strength exhibited by DK554 is of particular value.

A general description of the DK554 hybrid is presented in Table 2.

TABLE 2

MORPHOLOGICAL CHARACTERISTICS OF THE DK554 PHENOTYPE
(See Appendix)

| CHARACTERISTIC | DK554 VALUE* |
|---|---|
| 1. Seedling | |
| Percent Emergence | 92 |
| Color | Dark Green |
| Vigor 1-5 Rating | 3 |
| 2. Stalk | |
| Plant Height cm. | 247.2 |
| Ear Height cm. | 107.5 |
| Diameter (Width) cm. | 2.4 |
| Anthocyanin | Absent |
| Nodes with Brace Roots | 1.7 |
| Brace Root Color | Green |
| Internode Direction | Straight |
| Internode Length cm. | 18.4 |
| 3. Leaf | |
| Angle | Intermediate |
| Number | 18.9 |
| Post Poll Color | Dark Green |
| Length cm. | 84.3 |
| Width cm. | 9.7 |
| Sheath Anthocyanin | Absent |
| Sheath Pubescence | Heavy |
| Marginal Waves | Few |
| Longitudinal Creases | Absent |
| 4. Tassel | |
| Total Length cm. | 31.2 |
| Spike Length cm. | 22.0 |
| Peduncle Length cm. | 10.5 |
| Attitude | Compact |
| Branch Angle | Upright |
| Branch Number | 6.4 |
| Anther Color | Tan |
| Glume Color | Green |

TABLE 1

COMPARISON OF DK554 WITH 4 COMMERCIALLY SUCCESSFUL HYBRIDS

| | NTEST | SI % | YIELD | MOIST | SV | FGDU | PHT | EHT | BAR | SG | D % | STL | RTL | TNT | ESTR |
|---|---|---|---|---|---|---|---|---|---|---|---|---|---|---|---|
| DK554 | R 160 | 106.1 | 140.6 | 18.1 | 5.3 | 1362 | 83.7 | 37.5 | 0.6 | 4.6 | 0.2 | 5.6 | 0.7 | 57.2 | 103.7 |
| DK535 | | 105.9 | 139.5 | 17.9 + | 5.9 ** | 1352 + | 85.4 ** | 37.5 | 1.1 * | 3.3 ** | 0.5 ** | 3.2 ** | 2.7 ** | 58.1 | 103.5 |
| DK554 | F 90 | 109.6 | 148.8 | 18.4 | | | | | | | 0.4 | 4.7 | 0.2 | 53.7 | 103.9 |
| DK535 | | 103.1 ** | 142.1 ** | 17.9 ** | | | | | | | 0.5 | 5.1 | 0.7 * | 54.8 ** | 103.2 |
| DK554 | R 136 | 105.9 | 140.6 | 18.2 | 5.3 | 1356 | 83.7 | 37.8 | 0.6 | 4.7 | 0.2 | 5.6 | 0.7 | 57.6 | 103.7 |
| DK547 | | 97.6 ** | 134.5 ** | 19.0 ** | 5.7 ** | 1372 * | 84.7 | 39.4 ** | 1.0 + | 3.8 ** | 0.5 ** | 4.9 + | 2.4 ** | 58.2 | 104.6 |
| DK554 | F 79 | 109.1 | 152.9 | 18.6 | | | | | | | 0.5 | 5.0 | 0.2 | 53.7 | 104.0 |
| DK547 | | 102.6 ** | 136.8 ** | 19.0 ** | | | | | | | 0.6 | 4.2 | 0.3 | 55.1 ** | 104.8 |
| DK554 | R 160 | 106.1 | 140.6 | 18.1 | 5.3 | 1362 | 83.7 | 37.5 | 0.6 | 4.6 | 0.2 | 5.6 | 0.7 | 57.2 | 103.7 |
| PION3475 | | 99.3 ** | 136.5 ** | 19.3 ** | 5.4 | 1358 | 83.6 | 36.9 ** | 1.4 ** | 4.1 * | 0.6 ** | 5.0 + | 1.6 ** | 59.2 * | 105.4 |
| DK554 | F 24 | 108.6 | 137.5 | 18.1 | | | | | | | 0.5 | 4.6 | 0.1 | 53.3 | 103.6 |
| PION3475 | | 101.9 ** | 131.3 ** | 18.7 + | | | | | | | 0.7 | 3.5 | 0.1 | 55.6 ** | 104.8 |

Where
R = research test results
F = FACT testing
SI % = Selection index, see 67 in appendix.
Yield = see 68 in appendix.
Moist = see 69 in appendix.
SV = seedling vigor, a 1-9 rating of early season plant growth where 9 = best.
FGDU = energy required to flower (see 66 in this appendix).
PHT = see 6 in appendix.
EHT = see 41 in appendix.
BAR = % barren, % of plants that lack an ear.
SG = see 70 in appendix.
D % = see 71 in appendix.
STL = % of plants broken over below the ear at harvest.
RTL = % of plants leaning at greater than 30° angle to the ground.
TWT = see 65 in appendix.
ESTR = estimate of relative maturity (days) and significance levels are indicated as
+ = 10%
* = 5%
** = 1%

TABLE 2-continued
MORPHOLOGICAL CHARACTERISTICS OF THE DK554 PHENOTYPE
(See Appendix)

| CHARACTERISTIC | DK554 VALUE* |
|---|---|
| Glume Band | Absent |
| 5. Ear | |
| Silk Color | Tan |
| Number Per Stalk | 1.0 |
| Position (Attitude) | Upright |
| Length cm | 20.2 |
| Shape | Semi Conical |
| Diameter cm. | 4.3 |
| Weight gm. | 198.9 |
| Shank Length cm. | 15.8 |
| Shank Internode Number | 7.0 |
| Husk Bract | Short |
| Husk Cover cm. | 2.3 |
| Husk Opening | Intermediate |
| Husk Color Fresh | Green |
| Husk Color Dry | Buff |
| Cob Diameter cm. | 2.4 |
| Cob Color | Red |
| Cob Strength | Strong |
| Shelling Percent | 87.7 |
| 6. Kernel | |
| Row Number | 16.2 |
| Number Per Row | 43.9 |
| Row Direction | Curved |
| Type | Dent |
| Cap Color | Yellow |
| Side Color | Orange |
| Length (Depth) mm. | 11.9 |
| Width mm. | 7.8 |
| Thickness | 3.6 |
| Weight of 100K gm. | 294 |
| Endosperm Type | Normal |
| Endosperm Color | Yellow |
| 7. Other | |
| uniformity 1-5 Rating | 1 |
| GDUS to 50% Pollen Shed | 1223 |
| GDUS to 50% Silking | 1269 |

*These are typical of DK554 plants. Values may vary due to environment. Other values that are substantially equivalent are also within the scope of the invention. "Substantially equivalent" refers to quantitive traits that when compared do not show statistically significant differences of their means.

Genetic Markers to Identify Plants

Markers are genes, the phenotypic expressions of which are used to identify the presence of other genes or genetic complements which cosegregate with the markers through meiosis and appear jointly in offspring. Markers are generally codominant, that is, both alleles at a marker locus are readily detectable in a heterozygote. Markers which are useful in plant breeding comprise isozymes and restriction fragment length polymorphism (RFLP's). RFLP analysis has been performed on the parents of DK554 leading to the hybrid profile shown in Table 3.

Isozymes are forms of proteins that are distinguishable, for example, on starch gel electrophoresis, usually by charge and/or molecular weight. The isozyme profile of DK554 is shown in Table 4.

A standard set of loci may be used as a reference set. Comparative analysis of these loci may be used to compare the purity of hybrid seeds, to assess the increased variability in hybrids compared to inbreds, and to determine the identity of seeds, plants, and plant parts. In this respect, an isozyme or RFLP reference set may be partially used to develop genotypic "fingerprints."

Table 4 lists the identifying numbers of the alleles segregating at isozyme loci types for hybrid DK554. This set of alleles are one set of identifiers for the genetic complements of this hybrid. These alleles are not known to be directly related to the desirable traits of these hybrid plants (Goodman and Stuber, 1980), but are useful to identify genomes.

TABLE 3
ALLELES IN DK554 DETECTED BY RESTRICTION ENDONUCLEASE DIGESTION OF GENOMIC DNA FOLLOWED BY TREATMENT WITH PROBES

| Probe/Enzyme Combination | Allelic Pair |
|---|---|
| 0264H | GH |
| 0285E | — |
| 0306H | AA |
| 0445E | AB |
| 0B304E | — |
| 1120S | BD |
| 1234H | DK |
| 1236H | — |
| 1238H | EF |
| 1401E | AA |
| 1406H | AB |
| 1447E | — |
| 1447H | AA |
| 1B725E | BB |
| 2239H | — |
| 2297H | AC |
| 2298E | BC |
| 2402H | EE |
| 3212S | — |
| 3247E | — |
| 3257S | — |
| 3296H | AA |
| 3432H | DH |
| 3446S | — |
| 3457E | CE |
| 3B815H | BC |
| 4386H | DD |
| 4396E | AH |
| 4444H | AA |
| 4451H | BC |
| 4UMC19H | AB |
| 4UMC31E | BC |
| 4UMC31S | — |
| 5213S | AB |
| 5288E | — |
| 5288S | — |
| 5295E | CD |
| 5408H | AA |
| 5409H | CC |
| 5579S | — |
| 5UMC95H | AC |
| 6223E | CC |
| 6252H | AE |
| 6280HE | BC |
| 6373E | AE |
| 7263E | AC |
| 7391H | AC |
| 7392S | — |
| 74233E | — |
| 7455H | BB |
| 810S | CH |
| 8110S | AD |
| 8144E | BB |
| 8268H | AB |
| 8438E | AB |
| 8585H | — |
| 8B2369S | — |
| 8UMC48E | AC |
| 9209E | AA |
| 9322E | CG |
| 9266S | — |
| 9B713S | AB |
| 9BZE | AB |
| 9WAXE | AB |

*Probes used to detect RFLP's are from Native Plants Incorporated, 417 Wakar Way, Salt Lake City, Utah 84108. See EPO 306 139 A2:probes are currently available from Linkage Genetics, 1515 W. 2200 S., Suite C, Salt Lake City, Utah 84119.

TABLE 4

| ISOZYME GENOTYPE FOR HYBRID DK554 | |
|---|---|
| LOCUS | ISOZYME ALLELES |
| Acph1 | ⅔ |

TABLE 4-continued

ISOZYME GENOTYPE FOR HYBRID DK554

| LOCUS | ISOZYME ALLELES |
| --- | --- |
| Adh1 | 4 |
| Cat3 | 9 |
| Dia-1 | 8 |
| Dia-2 | 4 |
| Gdh-1 | 1 |
| Got-3 | 4 |
| Got-2 | 4 |
| Got-1 | 4 |
| Idh-1 | 4 |
| Idh-2 | 4/6 |
| MdH-1 | 1/6 |
| Mdh-2 | 3.5 |
| Mdh-3 | 16 |
| Mdh-4 | 12 |
| Mdh-5 | 12 |
| Pgm-1 | 9 |
| Pgm-2 | 4 |
| 6-Pgd-1 | 3.8 |
| 6-Pgd-2 | 5 |
| Phi-1 | 4 |
| Tpi-1 | 4 |
| Tpi-2 | 4 |
| Tpi-3 | 4 |
| Tpi-4 | 4 |
| # of Seeds Assayed | 6 |

Methods for In Vitro Hybrid Plant Regeneration

Hybrid plants can be grown from hybrid seeds by methods well known to those skilled in the art. Hybrid plants may also be regenerated from tissues of hybrid plants by use of in vitro laboratory methods of tissue culture.

In certain embodiments, recipient cells are selected following growth in culture. Where employed, cultured cells are preferably grown either on solid supports or in the form of liquid suspensions. In either instance, nutrients are provided to the cells in the form of media, and environmental conditions are controlled. There are many types of tissue culture media comprising amino acids, salts, sugars, hormones and vitamins. Most of the media employed to regenerate hybrid plants will have some similar components, the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to the N6 medium described by Chu, et al. (1975) and the MS media, Murashige and Skoog (1962). In an exemplary embodiment for preparation of recipient cells, modifications of these media are available. A preferred hormone for such purposes is dicamba or 2,4-D. However, other hormones may be employed, including NAA, NAA+2,4-D or perhaps even picloram. Modifications of these and other basic media may facilitate growth of recipient cells at specific developmental stages.

An exemplary embodiment for culturing recipient corn cells in suspension cultures includes using embryogenic cells in Type II (Armstrong and Green, 1985; Gordon-Kamm, et al., 1990) callus, selecting for small (10-30µ) isodiametric, cytoplasmically dense cells, growing the cells in suspension cultures with hormone containing media, subculturing into a progression of media to facilitate development of shoots and roots, and finally, hardening the plant and readying it metabolically for growth in soil.

Meristematic cells (i.e., plant cells capable of continual cell division and characterized by an undifferentiated cytological appearance, normally found at growing points or tissues in plants such as root tips, stem apices, lateral buds, etc.) may be cultured.

EXAMPLES

Example 1

Methods of Producing Hybrid Genetic Complements: Breeding

Corn plants (*Zea mays L.*) can be bred by either self-pollination or cross-pollination techniques. Corn has male flowers, located on the tassel, and female flowers, located on the ear, on the same plant. Natural pollination occurs in corn when wind blows pollen from the tassels to the silks that protrude from the tops of the incipient ears. Mechanical pollination may be effected either by controlling the types of pollen that can blow onto the silks or by pollinating by hand.

Two inbred lines were selected as parents of a hybrid genetic complement, one of which is the inbred line FBLL, the other LIBC4. These parental lines were planted in pollinating proximity to each other. This may be achieved by planting the parental lines in alternating rows, in blocks or in any other convenient planting pattern. The plants of both lines were allowed to grow until the time of flowering. Advantageously, during this growth stage, the plants are in general treated with fertilizer and/or other agricultural chemicals as considered appropriate by the grower.

At the time of flowering, in the event that inbred line LIBC4 is employed as the male parent, the tassels of the other parental line, FBLL are removed from all plants employed as the female parental line. The detasseling can be achieved manually but also can be done by machine if desired.

The lines are then allowed to continue to grow and natural cross-pollination occurs as a result of the action of wind which is normal in the pollination of grasses, including corn. As a result of the emasculation of the female parent line, all the pollen from the male parent line, e.g., LIBC4, is available for pollination because tassels, and thereby pollen bearing flowering parts, have been previously removed from all plants of the inbred line being used as the female in the hybridization. Of course, during this hybridization procedure, the parental varieties are grown such that they are isolated from other corn fields to prevent any accidental contamination of pollen from foreign sources. These isolation techniques are well within the skill of those skilled in this art.

Both of the parent inbred lines of corn are allowed to continue to grow until maturity, but only the ears from the female inbred parental lines are harvested to obtain seeds of a novel $F_1$ hybrid corn. If desired, corn produced in the male parent variety can be harvested, e.g., for grain use, but these seeds are not useful as hybrid seeds.

The novel $F_1$ hybrid seed produced may then be planted in a subsequent growing season with the desirable characteristics in terms of $F_1$ hybrid corn plants providing improved grain yields and the other desirable characteristics disclosed herein, being achieved.

Example 2

Methods of Producing Hybrid Genetic Complements: In Vitro Regeneration

Embryogenic calli are produced (Gordon-Kamm et al., 1990). Specifically, plants from hybrids produced from crossing the inbreds (FBLL×LIBC4) are grown to flowering in a greenhouse. (Cells from the inbred parental line FBLL have been cultured and regenerated plants. Hybrid lines such as DK554 are generally easier to culture and use for regeneration than inbred lines, therefore, successful regeneration of the parent predicts successful regeneration of DK554.) Explants from at least one of the following F$_1$ tissues: immature tassel tissue, intercalary meristems and leaf bases, apical meristems, and immature ears, are placed in an initiation medium which contain MS salts, supplemented with thiamine, agar, and sucrose. Cultures are incubated in the dark at about 23° C. All culture manipulations and selections are performed with the aid of a dissecting microscope.

After about 5-7 days, cellular outgrowths are observed from the surface of the explants. After about 7-21 days, the outgrowths are subcultured by placing them into fresh medium of the same composition. Some of the intact explants are placed on fresh medium.

Several subcultures later (after about 2 to 3 months) enough material is present from explants for subdivision of these embryogenic calli into two or more pieces. Callus pieces from different explants are not mixed. After further growth and subculture (about 6 months after embryogenic callus initiation), there are usually between 1 and 100 pieces derived ultimately from each selected explant. During this time of culture expansion, a characteristic embryogenic culture morphology develops as a result of careful selection at each subculture. Any organized structures resembling roots or root primordia are discarded. Any material known from experience to lack the capacity for sustained growth is also discarded (translucent, watery, embryogenic structures). Structures with a firm consistency resembling at least in part the scutellum of the in vivo embryo are selected.

The callus is maintained on agar-solidified MS-type media. The hormone used is 2,4-D. Visual selection of embryo-like structures is done to obtain subcultures. Transfer of material other than that displaying embryogenic morphology results in loss of the ability to recover whole plants from the callus.

Some calli will exhibit somaclonal variation. These are phenotypic changes appearing in culture.

Cell suspensions are prepared from the calli by selecting cell populations that appear homogeneous macroscopically. A portion of the friable, rapidly growing embryogenic calli is inoculated into MS Medium. The calli in medium are incubated at about 27° C. on a gyrotary shaker in the dark or in the presence of low light. The resultant suspension culture is transferred about once every seven days by taking about 5 to 10 ml of the culture and introducing this inoculum into fresh medium of the composition listed above.

For regeneration, embryos which appear on the callus surface are selected and regenerated into whole plants by transferring the embryogenic structures into a sequence of solidified media which include decreasing concentrations of 2,4-D or other auxins. Other hormones which may be used in the media include dicamba, NAA, ABA, BAP, and 2-NCA. The reduction is relative to the concentration used in culture maintenance media. Plantlets are regenerated from these embryos by transfer to a hormone-free medium, subsequently transferred to soil, and grown to maturity.

Progeny are produced by taking pollen and selfing, backcrossing or sibbing regenerated plants by methods well known to those skilled in the art. Seeds are collected from the regenerated plants by methods known to those of skill in the art.

While the invention is susceptible to various modifications and alternative forms, specific embodiments thereof have been shown by way of examples and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

---

APPENDIX: PLANT TRAIT DESCRIPTIONS

2. Seedling Emergence - Number of emerged plants divided by number of seeds planted, expressed as a percentage.
3. Seedling Height - Plant height at the 6-8 leaf stage in centimeters.
4. Seedling Color - Color of leaves at the 6-8 leaf stage (light green, dark green, anthocyanin).
5. Seedling Vigor - Rated on a scale of 1-5 (1 = best) at the 2-4 leaf stage.
6. Plant Height - Measured from soil to the tip of the tassel in centimeters.
7. Stalk Diameter - Diameter of the lowest visible internode, measured in centimeters.
8. Stalk Anthrocyanin - Rated 1-2 weeks after pollination as absent, basal-weak, basal-strong, weak, strong.
9. Stalk Nodes with Brace Roots - Average number of nodes having brace roots on each plant.
10. Stalk Brace Root Color - Color of brace roots observed 1-2 weeks after pollination (green, red, or purple).
11. Stalk Internode Length - Length of the internode above the primary ear in centimeters.
12. Stalk Internode Direction - Observed after pollination, straight or zig-zag.
13. Leaf Angle - Angle of the upper leaves to the stalk; 0-30° = upright, 30-60° = intermediate, 60-90° = lax.
14. Leaf Number - Total number of leaves from the cotyledon leaf to the flag leaf.
15. Leaf Length - Length of the primary ear leaf measured in centimeters.
16. Leaf Width - Width of the primary ear leaf measured at the widest point in centimeters.
17. Leaf Color - Color of the leaves 1-2 weeks after pollination. (Light green, medium green, dark green, very dark green).
18. Leaf Marginal Waves - Rated for waves on the leaf margin 1-2 weeks after pollination (none, few, many).
19. Leaf Longitudinal Creases - Rated for creases on the leaf surface 1-2 weeks after pollination (absent, few or many).
20. Leaf Sheath Anthocyanin - Rated 1-2 weeks after pollination (absent, basal-weak, basal strong, weak, strong).
21. Leaf Sheath Pubescence - Rated 1-2 weeks after pollination (light, medium or heavy).
22. Tassel Length - Measured from the base of the bottom tassel branch to the tassel tip in centimeters.
23. Tassel Spike Length - Measured from the base of the top tassel branch to the tassel tip in centimeters.
24. Peduncle Length - Measured from the base of the flag leaf to the base of the bottom tassel branch in centimeters.
25. Tassel Branch Number - Number of primary tassel branches.
26. Tassel Branch Angle - Angle of an average tassel branch to the main stem of the tassel; less than 30 ° = upright, 30-45° = intermediate, greater than 45° = lax.
27. Tassel Attitude - Observed after pollination as open or

APPENDIX: PLANT TRAIT DESCRIPTIONS (continued)

compact.
28. Tassel Glume Color - Color of glumes at 50% shed (green, red or purple).
29. Tassel Glume Band - Closed anthocyanin ring at base of glume (absent or present).
30. Tassel Anther Color - Color of anthers at 50% shed (green-yellow, yellow, pink, red, purple).
31. 50% Shed Standard GDUS - Standardized DGUS are adjusted for the location and year affects (1989 DeKalb factor = −115. 1989 Illiopolis factor = +24).
32. 50% Silk Standard GDUS - Standardized GDUS are adjusted for the location and year affects (1989 DeKalb factor = −115, 1989 Illiopolis factor = +24).
33. Uniformity - Rated throughout the growing season based on variability in plant and ear height, tassel type, anther and silk color (scale of 1–5; 1 = best).
34. Husk Bract - Length of an average husk leaf (short, medium or long).
35. Husk Cover - Distance from the tip of the ear to the tip of the husks (exposed ear = 0.0).
36. Husk Opening - Husks are rated for the tightness at harvest stage (tight, intermediate or open).
37. Husk Color Fresh - Color of husks 1–2 weeks after pollination (green, red or purple).
38. Husk Color Cry - Color of husks at harvest stage (buff, red or purple).
39. Shank Length - Length of the ear shank measured in centimeters.
40. Shank Internode Number - Number of internodes on the ear shank.
41. Ear Height - Measured from the soil to the base of the primary ear in centimeters.
42. Ears/Stalk - The number of ears with grain on each plant.
43. Ear Silk Color - Color of silk observed 2–3 days after silks emerge (green-yellow, yellow, pink, red, purple).
44. Ear Position - Rated at harvest stage (upright, horizontal, pendent).
45. Ear Weight - Weight of the ear expressed in grams.
46. Ear Length - Length of the ear measured in centimeters.
47. Ear Diameter - Diameter of the ear at the midpoint measured in centimeters.
48. Ear Shape - Observed as conical, semi-conical or cylindrical.
49. Kernel Row Number - Number of rows on one ear.
50. Kernel Row Direction - Observed as straight, slightly curved, spiral or indistinct (scattered).
51. Kernel Number per Row - Number of kernels in one row.
52. Kernel Cap Color - Color of the kernel cap observed at dry stage (white, lemon-yellow, yellow, orange).
53. Kernel Side Color - Color of the kernel side observed at dry stage (white, pale yellow, yellow, orange, red, brown).
54. Kernel Endosperm Type - Observed as normal, waxy, opaque.
55. Kernel Endosperm Color - Observed as white, pale yellow, yellow.
56. Kernel Weight/1000k - Weight of 1000 kernels expressed in grams.
57. Kernel Length - Distance from the cap to the pedicel measured in millimeters.
58. Kernel Width - Distance across the flat side of the kernel measured in millimeters.
59. Kernel Thickness - Distance across the narrow side of the kernel measured in milimeters.
60. Kernel Type - Observed as dent, flint, intermediate.
61. Cob Diameter - Diameter of the cob at the midpoint measured in centimeters.
62. Cob Strength - Cobs are mechanically broken and rated as either strong or weak.
63. Cob Color - Color of the cob (white, pink, red, brown, purple).
64. Shelling Percentage - Shelled grain weight divided by the sum of grain and cob weight, expresses as a percentage.
65. Test Weight - U.S. Government standards are that 56 lbs equals 1 bushel, with a 15% moisture content.
66. GDU Shed - The number of growing degree units (GDU) required for an inbred line or hybrid to shed pollen from the time of planting.

$$GDU = \frac{[(Max + Min) \text{ daily temperature } °F.]}{2} - 50° F.$$

Where maximum daily temperature must not exceed 85° F. and minimum must not be below 50° F.
67. Selection Index - A single measure of a hybrid's relative worth based on information for up to five traits (always includes yield).
68. Yield - Actual bushels/acre at harvest adjusted to 15.5% moisture.
69. Moisture - Percent moisture of the grain at harvest.
70. Staygreen - A measure of plant health at the time of maturity of the ear leaves.
71. Dropped Ears - The percent of plants that did not drop ears prior to harvest.

REFERENCES

The references listed below are incorporated herein by reference to the extent that they supplement, explain, provide a background for, or teach methodology, techniques, and/or compositions employed herein.

Reference 1. Armstrong and Green, (1985). "Establishment and Maintenance of Friable, Embryogenic Maize Callus and the Involvement of L-Proline," Planta, 164:207–214.
Reference 2. Asins, M. J. (1988) "Detection of Linkage Between Restriction Fragment Length Polymorphism Markers and Quantitative Traits," Theor. App. Genet. 76:623–626.
Reference 3. Beckmann, J. S. and Soller, M. (1983) "Restriction Fragment Length Polymorphisms in Genetic Improvement: Methodologies, Mapping and Costs, "Theor. Appl. Genet. 67:35–43.
Reference 4. Burr, B., Evola, E., Burr, F., et al. (1983) "The Application of Restriction Fragment Length Polymorphisms to Plant Breeding," Settoco, J. K. and Hollaender, A. (eds.) Genetic Engineering and Principles and Methods, Plenum Press, N.Y. and London. pp. 45–59.
Reference 5. Chu, C. C., Wang, C. C., Sun, C. S., et at. (1975). Scientia Sinica 18:659–668.
Reference 6. Coe, E. H., et at (1988) "The Genetics of Corn and Corn Improvement", 3rd. ed., Vol. 18, Sprague and Dudley (eds) 87:258
Reference 7. Duvick, D. N. (1985) "Genetic Contribution to Yield Gains of U.S. Hybrid Maize - 1930–1980," Genetic Contribution to Yield Gains of Five Major Crops, pp. 15–48.
Reference 8. Evola, S. V., Burr, J. A., and Burr, B. (1986) "The Suitability of Restriction Fragment Length Polymorphisms as Genetic Markers in Maize." Theor. App. Genet. 71:765-771.
Reference 9. Falconer, D. S. (1960) "Introduction to Quantitative Genetics," Ronald Press Co., New York.
Reference 10. Goodman, M. and Stuber, C. (1980), "Genetic Identification of Lines and Crosses Using Isoenzyme Electrophoresis," Proceedings of the Thirty-Fifth Annual Corn and Sorghum Industry Research Conferences, Chicago, 1980.
Reference 11. Gordon-Kamm, W. et al., (1990) "Transformation of Maize Cells and Regeneration of Fertile Transgenic Plants," The Plant cell, V. 2, 603–618.
Reference 12. Helentjaris, T., King, G., Slocu, M., et al. (1985) "Restriction Fragment Polymorphisms as Probes for Plant Diversity and Their Developments as Tools for Applied Plant Breeding," Plant Mol. Biol. 5:109–118.
Reference 13. Helentjaris, T., Slocum, M. Wright, S., et al., (1986) "Construction of Genetic Linkage Maps in Plant Using Restriction Fragment Polymorphisms," Theor. Appl. Genet. 72:761-769.
Reference 14. Lande, R. and Thompson, R. (1990) "Efficiency of Marker-Associated Selection in the Improvement of Quantitative Traits," Genetics 124:743–756.
Reference 15. Lander, E. S. and Botstein, D. (1989) "Mapping Mendelian Factors Underlying Quantitative Traits Using RFLP Linkage Maps," Genetics 121:185–199, see also WO 90104651.
Reference 16. Murashige, T. and Skoog, F. (1962). Plant Physiol. 15:473–497.
Reference 17. Paterson, A. H., et al. (1988) "Resolution of Quantitative Traits into Mendelian Factors by Using a Complete Linkage Map of Restriction Fragment Polymorphism," Nature 335:721-724.
Reference 18. Rhodes, C. A., Pierce, D. A., Mettler, F. J., et al. (1988). Science 240:204–207.
Reference 19. Sprague, G. F. and Eberhart, S. A. (1977) "Corn Breeding," in Corn and Corn Improvements, J. A. Dudley and G. F. Sprague (eds), Iowa State Univ. Press.
Reference 20. Troyer, A. F. (1990) "A Retrospective View of Corn Genetic Resources", Journal of Heredity, 81:17–24.
Reference 21. EP 0 306 139 A2, "Identification, Localization and Introgression into Plants of Desired Multigenic Traits."
Reference 22. PCT/US89/00709, "Genetic Linkages Between Agronomically Important Genes and Restriction Fragment Length Polymorphisms."

What is claimed is:

1. A hybrid corn plant designated DK554 formed by the crossing of inbred corn plants FBLL and LIBC4.

2. A seed of the corn plant according to claim 1.

3. A hybrid corn plant having all phenotypic and morphological characteristics of the corn plant according to claim 1.

4. A tissue culture of regenerable cells from DK554.

* * * * *